United States Patent
Lukhard et al.

[11] Patent Number: 5,110,517
[45] Date of Patent: May 5, 1992

[54] METHOD FOR DEREGISTERING CRIMPED MULTIFILAMENT TOW

[75] Inventors: Craig R. Lukhard, Newark; Jerry F. Potter, Seaford, both of Del.; Maurice C. Todd, Chadds Ford, Pa.

[73] Assignee: E. I. DuPont de Nemours and Company, Wilmington, Del.

[21] Appl. No.: 531,654

[22] Filed: Jun. 1, 1990

[51] Int. Cl.⁵ ............................................. D02J 1/12
[52] U.S. Cl. ........................ 264/40.1; 19/0.46; 19/65 T; 28/241; 28/248; 264/168; 264/290.5; 264/290.7
[58] Field of Search .............. 264/40.1, 290.5, 290.7, 264/168; 19/240, 242, 65 T, 0.46; 28/241, 248

[56] References Cited

U.S. PATENT DOCUMENTS

| | | | |
|---|---|---|---|
| 2,581,922 | 1/1952 | Spencer | 264/290.7 |
| 3,143,784 | 8/1964 | Scott | 28/72 |
| 3,271,943 | 9/1966 | Williams, Jr. | 57/140 |
| 3,465,399 | 9/1969 | Sokolowski et al. | 28/1 |
| 3,549,741 | 12/1970 | Caison et al. | 264/210 |
| 4,404,718 | 9/1983 | Tajiri et al. | 28/241 |
| 4,501,710 | 2/1985 | Abbott et al. | 264/290.5 |

Primary Examiner—James Lowe

[57] ABSTRACT

A method and apparatus for deregistering drawn crimped nylon multifilament tow includes the steps of stretching the tow under constant controlled tension at a temperature below the glass transition temperature of the nylon. The apparatus includes means for sensing the tension of the tow between the feed and draw sections of a stretching device and producing a signal representative of the tension sensed and a controller for changing the speed of the draw section actuated by said signal.

4 Claims, 2 Drawing Sheets

METHOD FOR DEREGISTERING CRIMPED MULTIFILAMENT TOW

BACKGROUND OF THE INVENTION

This invention relates to a method and apparatus for deregistering crimped multifilament polyamide tow and the product produced by this method and, more particularly, it relates to maintaining the tension on the crimped tow substantially constant during the stretching operation used to deregister the crimped tow.

It is known to crimp synthetic filaments; however, when high degrees of crimp are imparted to the tow for particular end uses and the tow is then cut to staple, this high crimp level actually inhibits further processing because the staple produced exhibits excessive cohesion and, as a consequence, the cut staple segments are difficult to process in worsted and woolen systems to make yarns. More particularly, when such fibers are carded to comb them to parallelism they may, because of the excessive cohesion, be entangled to such a degree that portions of the fibers are stretched until crimp is removed permanently or the filaments break. It is known that by deregistering the tow by stretching, i.e. redrawing at a fixed draw ratio, cohesion is reduced and mill processing of staple cut from the tow improves. However, when deregistering takes place using crimped tow made in a so-called split process where the ends of crimped tow are joined to accommodate a continuous cutting and baling operation, the joined regions cannot be elongated during stretching to deregister the tow and, consequently, filaments break or perhaps the tow itself will break causing a disruption in the process. In addition, local variations in crimp level associated with stops and starts of a draw line, small changes in moisture content or temperature, or storage conditions for split process product are continuously occurring and, therefore, adjustments in tension are continuously needed to maintain final product uniformity.

SUMMARY OF THE INVENTION

To overcome the above-noted deficiencies and produce a more uniform product and in accordance with the present invention, an enhanced method and apparatus for producing a deregistered crimped polyamide tow is provided which comprises stretching by redrawing drawn crimped polyamide tow at a temperature below the glass transition temperature of the polyamide at conditions of operation and under controlled substantially constant tension. Following stretching at controlled tension, the tow may be cut into staple or packaged as tow. Tension levels are maintained in the range of from about 0.05 to about 0.80 grams/denier and preferably in the range of from about 0.10 to about 0.30 grams/denier.

A preferred feed product is stuffer box crimped and steam annealed nylon tow or staple having a denier per filament of 6 to 24 and a crimp level of 6-20 crimps per inch with a crimp elongation of 25 to 45%. After stretching by redrawing, the crimp will be reduced to 15 to 35% crimp elongation for optimum mill processing. Performance and quality of stretched product are substantially improved and less crimp will be lost through carding and subsequent mill processing, thereby increasing the crimp recovery and without loss of bulk of the yarn in the final product in the preferred range.

The redrawing operation of this invention which reduces the apparent crimp (i.e., % crimp elongation after redrawing) in the product does not result in a loss of retained crimp (i.e. % crimp elongation) in final spun and twistset yarns; it in fact enhances it. This is attributed to the uniform nature of crimp reduction accomplished during redrawing versus the random reduction which occurs in carding and subsequent mill processing.

DETAILED DESCRIPTION OF THE DRAWING

Figure 1:
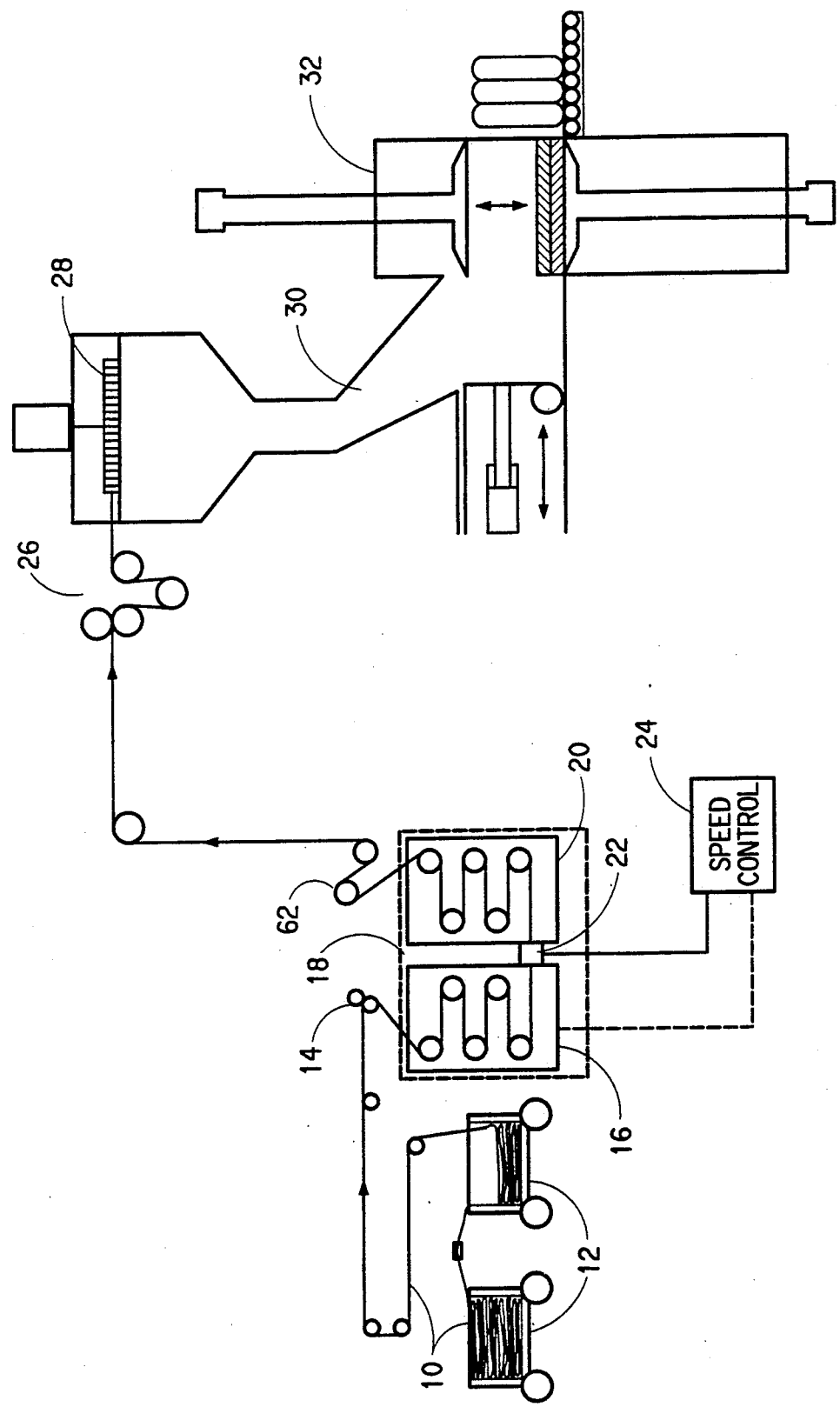
FIG. 1 is a schematic illustration of the steps of deregistering crimped tow by stretching, then cutting the tow, and baling the cut tow.

In the embodiment chosen for purposes of illustration, crimped nylon tows 10 are taken from storage containers 12 and passed through guide rollers 14 to feed rolls 16 of stretching apparatus 18 and then to draw rolls 20. A tension transducer 22 (model UPB-10-MWF2500 by Cleveland Kidder Co.) is located between feed rolls 16 and draw rolls 20 to monitor tension and transmit a signal speed control unit 24 for feed rolls 16. After stretching the tow enters a powered puller section 26 which provides a stable tension to cutter 28 where tow is cut to a desired fiber length, normally 4.0 to 8.0 inches for carpet fibers. The cut staple descends via chute 30 to the entrance of a baler 32. Tow which is packaged as tow goes directly to a storage device (not shown) from puller section 26.

Figure 2:
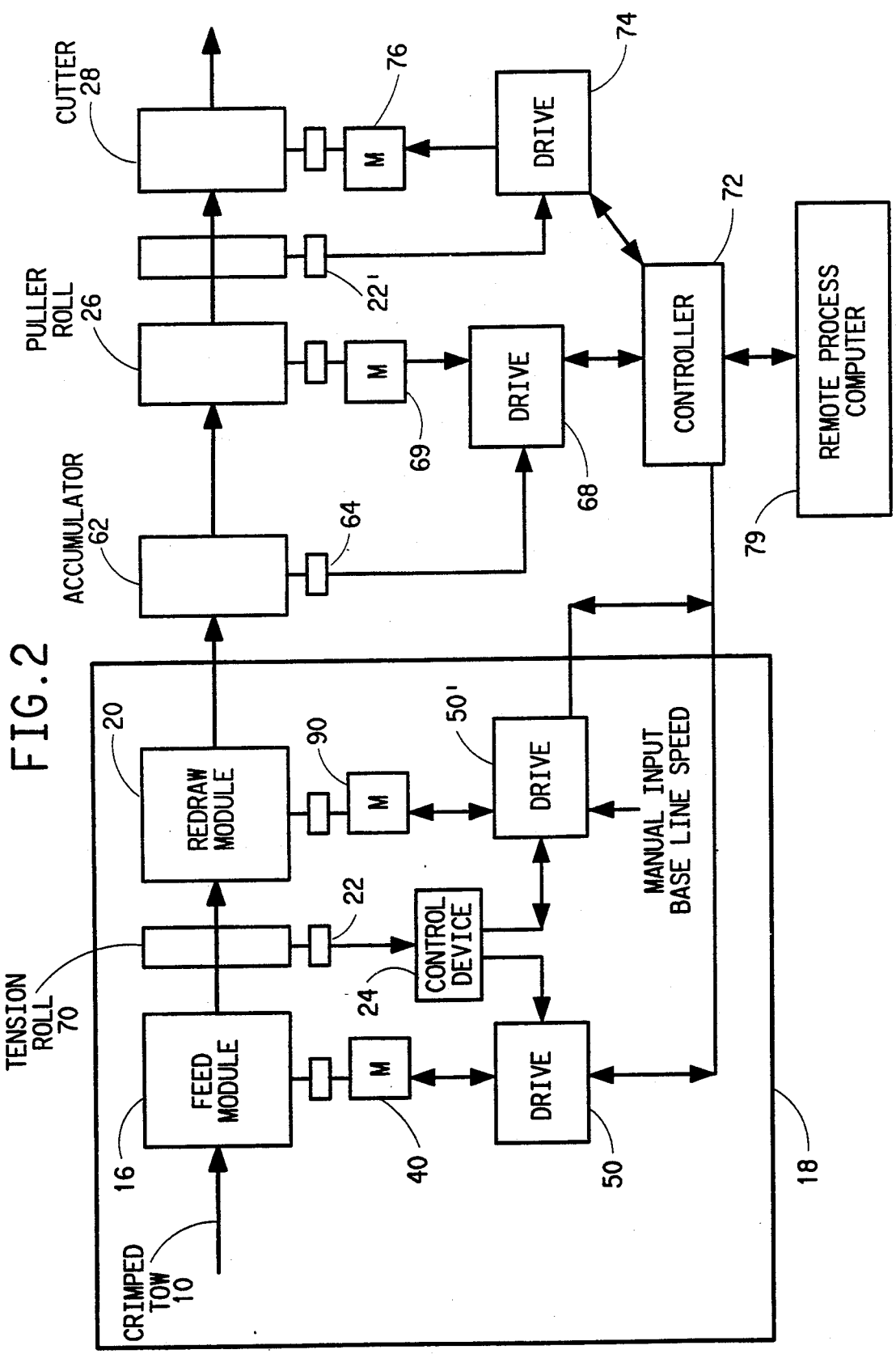
FIG. 2 is a schematic illustration of the means for controlling the tension during deregistration at a substantially constant level.

FIG. 2 illustrates the control system for controlling tension during deregistration wherein crimped tow 10 is fed to a stretching apparatus or deregistering unit 18 comprising a feed module 16 containing a plurality of smooth surfaced chrome plated rolls 16 geared together and all driven by a variable speed DC motor 40 and Reliance Maxi Pac solid state drive 50. As the tow exits the feed module and enters the redraw module 20, it passes over a tension monitoring roll 70 which is mounted on Cleveland Kidder model UPB-10-MWF-2500 tension transducer 22. The redraw module 20 also contains a plurality of smooth chrome plated rolls all geared together and driven at the same speed by a variable speed DC motor 90 and controlled by a Reliance Maxi Pac solid state drive 50'. The speed of the motor 90 is preset to a desired rate and the speed of the feed module motor 40 is modulated through an Avtron PDC-5 drive control device 24 and the feed module solid state drive 50' based on the tension measurements from transducers 22. Any deviations in infeed tension due to crimp variations or defects in the product such as a joined section are instantly sensed and the speed of the feed module 16 is adjusted to maintain constant tension. The drive module controller 24 is capable of both speed and tension control to facilitate ease of startup. Tension control is the preferred mode of operation for optimum product uniformity.

An accumulator 62 is located at the discharge of the redraw module 20 and it contains a speed control device 64 on the floating roll which regulates the speed of puller rolls 26 through its drive 68 and motor 69. The speed of a cutter 28 downstream of the puller roll is regulated to maintain constant tension between the puller roll 66 and cutter 28. A tension sensor 22' located at the discharge of the puller section 26 is used to regulate the speed of the cutter drive 74 and its motor 76. Operation of the entire line is supervised by an Allen Bradley PLC-5-15 controller 72 which interfaces with a process computer 79.

In split processes where joined sections are used to connect tow between containers, tension control avoids over-extending the product in these sections. The control system is also capable of reducing tension to process these sections. A detection plate (not shown) connected to a limit switch detects large deviations in cross section, a signal is sent to the controller 24 and tension is reduced to a preset level of ~0.10 gpd until the splice exits and is detected by a similar plate at the exit. If tension variations are detected due to regions of low or high crimp, a signal is sent to the control device 24 which feeds back an input signal to the feed section drive 50 and infeed speed is reduced or increased to maintain constant tension on the tow. Local variations in crimp level associated with stops and starts of a draw line, small changes in moisture content or temperature, or storage conditions for split process product are continuously occurring and, therefore, adjustments in tension are continuously made to maintain final product uniformity.

TEST METHODS

Crimp

A conventionally accepted method for characterization of crimped products in both filament and tow configurations can be explained by the following diagram:

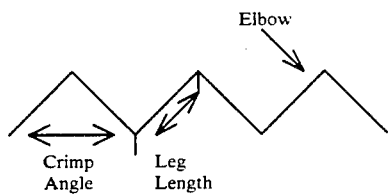

In this analysis the leg length (L) is the distance between midpoints of the bends in the filament. The elbow (E) is the midpoint of the filament bend. The crimp angle (CA) is the angle formed by the two legs on either side of an elbow. The crimp/inch is equal to one half the number of leg lengths in an inch of filament (an inch is measured when the filament is straightened out. Crimps per inch are measured by counting the total number of elbows in an inch of straightened filament and dividing by two. Crimp is the combination of crimp/inch (leg length) and crimp angles which make textured yarn different from normal drawn yarn. Crimp elongation is measured by hanging a length of crimped yarn under an added load of ~0.1 grams per denier for a fixed period varying from several seconds to a minute and an extended length ($L_e$) is determined. The load is then removed and the retracted length is determined ($L_r$) after waiting again for a specified period as stated. The percent crimp elongation (CE) is calculated as:

$$CD = [(L_e - L_r)/L_e] \times 100\%$$

Entanglement Assessment

A method for determination of crimp properties which establishs a measure of performance potential through a staple conversion operation can be achieved by use of the Spinlab Co. model 580 machine. This unit processes a small sample of cut product and measures the power to form it into a sliver similar to that achieved by conventional carding, the first step in a mill process for conversion of staple products back to spun yarns.

The mode of operation is as follows:

1. Cut 3 grams of product to a uniform length of 3 inches ±0.2 inch under a tension of 0.02 to 0.04 grams per denier tension. 2. Set rotoring to the following operating conditions Feed wheel speed—5 rpm
   Opener speed—4,000 rpm
   Rotor speed—10,000 rpm
   Rotor vacuum—25 inches water gauge.

3. Process 3 gram sample through system to form a uniform sliver sample.

4. Record sample and using power monitor record the energy to process a uniform section of tow for 30 seconds.

5. When initialized, the power monitor totalizes the power consumer over the 30 second interval and reports the results in Joules/1000 on a digital display meter.

6. Repeat analysis for 5 samples and average and standard deviation of results.

Results of this type of analysis show that the power consumption is substantially reduced by use of this invention. This reduction in power translates to the potential for both better yarn evenness, higher processing rates and a considerable reduction in fiber breakage, a major contributor to poor yarn evenness and low strength.

Fiber Opening Test

The Fiber Opening Test is a test using a standard commercially available fiber opening device similar to those used in carpet mills on blending and opening lines to assess the processing rates and overall quality of crimped staple products.

A 36 inch wide Fiber Controls Feeder model M-6 Syncro-Feeder equipped with a sargent comb on the hopper side and a rotary doffer on the discharge side of the lift apron was used for this test. The unit illustrated in FIG. 1 contains a feed hopper 1 of approximately 2 cubic feet, a wood slat floor apron 2, a lift apron 3 containing pin lagged flats with 0.6875 inch long pins spaced 1.5 inches on center across the flats. Flat to flat spacing is 1.75 inches and the pins are inclined at a 15° angle facing up. A variable speed drive is provided to allow lift apron speeds to be controlled from 10 to 100 feet per minute surface speed. The floor apron is driven from the lift apron and is operated at one third the lift apron surface speed. On the hopper side of the opener, an oscillating comb is provided to level fiber on the lift apron. The comb is gauged 2.0 inches off the apron and its stroke is adjusted to move from horizontal to 30° below the horizontal with a surface speed of 2× the lift apron. On the discharge side of the device, a rotary doffer is provided with brushes. This device operates at the surface speed of the apron and the brushes are gauged to intersect with the teeth on the apron. A watt meter is provided to monitor overall drive load and help establish maximum rate.

Evaluation of opening rates is done by conducting a series of throughput tests for 5 minute periods at a range of speeds. The feed hopper is filled between trials to insure constant pressure against the lift apron. A curve of performance is plotted and the maximum rate obtained is established as well as the power consumption at this rate. For most carpet fibers, the maximum rate is around 60 feet per minute apron speed; at higher speed throughput rates drop due to apron loading. All tests are duplicated and rates averaged. Bulk density of the product fed and delivered to the opener is established in a 16 cubic foot container as is the average clump weight of tufts fed and delivered for an overall performance potential assessment.

30" Spun Yarn Shrinkage Method

1. Cut 20-30 inch long lengths of spun yarn from a bobbin (yarn cuts are fully relaxed, not stretched, but with kinks straightened out). Provide uniform and even tension to all segments. A load of 1 gram per 10 denier is recommended.
2. Label and tie (loosely) the 20 cut ends and wrap in cheese cloth.
3. Place in boiling water for 30 minutes.
4. Remove from boiling water, rinse, gently squeeze out excess water (do not wring out).
5. Remove from cheese cloth, hang and air dry.
6. Remeasure each cut length under same load as original measurement (no tension).
7. Calculate shrinkage as follows:

$$\frac{\text{Original length} - \text{final length} \times 100}{\text{Original length}} = \% \text{ Shrinkage}$$

Work to Remove Crimp Method

Objective
Assess the durability of a product to retain crimp through staple processing.
Equipment
Instron model 1122
1,000 pound load cell (tow)
1,000 gram load cell (single filament)
Instron "CATS" software package
Samples
Tow—gauge length 6 inches
Single filament—any cut length from bale sample
Mode of Operation
1. Measure and record tow or filament properties for crimped product using Instron.
2. Use work to remove crimping grams per denier as reported by Instron "CATS" program to assess crimp durability of product.
3. Repeat analysis for 3 tow samples and 10 single filament samples and report mean and standard deviation for all analysis.

EXAMPLES

The following examples are illustrative of the present invention and of the best mode presently contemplated of carrying out the invention, but the invention is not to be interpreted as limited to all details of the examples.

In the example of the table below, an 18 denier per filament, trilobal, drawn and steam crimped nylon 66 tow was produced at 35% crimp elongation (CE) and 9.3 crimp per inch. This tow was redrawn at constant tension, cut and baled on a remote processing line. Item A was run as a control without redrawing and items B and C were run to illustrate the value of this invention on product performance and final value. Item A was cut directly without redrawing and the only tension the tow was subjected to was a 0.03 gpd tension at the cutter for cut length control. Items B and C were stretched to tensions of 0.25 and 0.70 gpd. A commercial cutter was coupled to the redraw device and all products were cut and fed to a commercial baler where they were pressed, wrapped and strapped to a density of 20 pounds per cubic feet.

Further details from the process from spinning through baling and performance as well as product properties of the yarn before and after mill process from the bale to spun and twisted yarn are shown in the example below.

TABLE

| Item | A (Control) | B | C |
|---|---|---|---|
| Crimping conditions | | | |
| crimp elongation (% CE) | 34 | 34 | 34 |
| crimp per inch | 9.3 ± .3 | 9.3 ± .3 | 9.3 ± .3 |
| Redraw conditions | | | |
| tow inlet temperature °C. | 28 ± 1 | 28 ± 1 | 28 ± 1 |
| redraw tension gpd | 0.00 | 0.25 | 0.70 |
| apparent crimp (% CE - after redraw) | 34 | 25 | 19 |
| work to remove crimp redrawn gpd (1) | 0.618 | 0.617 | 0.580 |
| Mill processing conditions | | | |
| twist set method | Superba | Superba | Superba |
| twist set temperature °C. | 132 ± 1 | 132 ± 1 | 132 ± 1 |
| opening rate (3) | 450 | 630 | 876 |
| Spin Lab Rotoring Power (Joules) (2) | 37 | 24 | 18 |
| 30" yarn shrinkage (4) | 16.4 | 17.5 | 13.9 |
| card sliver CV (Uster %) (5) | 8.8 | 7.9 | 6.5 |
| pin sliver CV (Uster %) (5) | 10.7 | 9.3 | 8.2 |
| retained crimp (% CE - in final set yarn) | 8.4 | 8.9 | 8.6 |
| singles yarn sliver CV (tester %) (5) | 25.3 | 24.7 | 23.6 |

(1) Instron work to remove crimp analysis using "CATS" software package.
(2) Entanglement assessment - Spinlab co. Rotoring Unit with Power Monitor.
(3) Du Pont opening test - see procedure at 52.5 fmp apron speed.
(4) Du Pont 30" single yarn shrinkage test - attached.
(5) Uster Co. Capactive Evenness Tester
singles yarn (100 ypm, 12.5 minute run time, average of readings at 30 second intervals for 5 samples
sliver samples (run at 25 ypm, run time 2.5 minutes per sample - average 5 sample.

Highly crimped and annealed yarn as produced have advantages in the final spun and twistset yarns. However, as is illustrated, mill performance and yarn quality of highly annealed yarns are poor unless the product has post crimp enhancement as is provided by use of this invention. It is also obvious that the redrawing operation which reduces the apparent crimp, i.e., % crimp elongation after redrawing, in the product does not result in a loss of retained crimp, i.e. % crimp elongation, in final spun and twistset yarns; it in fact slightly enhances it. This is attributed to the uniform nature of crimp reduction accomplished during redrawing versus the random reduction which occurs in carding and subsequent mill processing.

What is claimed is:

1. A method for deregistering a drawn crimped polyamide multifilament tow having variations of physical properties along the length of the tow comprising stretching said tow under a predetermined tension between feed and draw rolls and maintaining said tension substantially constant by controlling the speed of said feed rolls to maintain said tension constant while stretching sections of tow with differing physical properties.

2. The method of claim 1 wherein said stretching step is at a temperature below the glass transition temperature of the tow.

3. The method of claims 1 or 2 wherein said predetermined tension is in the range of from about 0.05 to about 0.80 grams/denier.

4. The method of claims 1 or 2 wherein said predetermined tension is in the range of from about 0.10 to about 0.30 grams/denier.

* * * * *